United States Patent [19]

Mahurkar

[11] Patent Number: 5,378,230
[45] Date of Patent: Jan. 3, 1995

[54] TRIPLE-LUMEN CRITICAL CARE CATHETER

[76] Inventor: Sakharam D. Mahurkar, 6171 N. Sheridan Rd., #1112, Chicago, Ill. 60660

[21] Appl. No.: 146,478

[22] Filed: Nov. 1, 1993

[51] Int. Cl.$^5$ ............................................. A61M 3/00
[52] U.S. Cl. ........................................ 604/43; 604/53; 604/264
[58] Field of Search ................ 128/656, 657, 658; 604/53, 170, 264, 280, 282, 43, 80; 606/194

[56] References Cited

U.S. PATENT DOCUMENTS

| | | |
|---|---|---|
| Re. 31,873 | 4/1985 | Howes . |
| 4,733,669 | 3/1988 | Segal ................................. 604/96 |
| 4,795,439 | 1/1989 | Guest ................................ 604/264 |
| 4,995,865 | 2/1991 | Gahara et al. ..................... 604/280 |
| 5,108,369 | 4/1992 | Ganguly et al. ................... 604/280 |
| 5,190,520 | 3/1993 | Fenton, Jr. et al. ............... 604/282 |
| 5,195,962 | 3/1993 | Martin et al. ..................... 604/164 |
| 5,221,255 | 6/1993 | Mahurkar et al. . |
| 5,221,256 | 6/1993 | Mahurkar . |

*Primary Examiner*—John D. Yasko
*Attorney, Agent, or Firm*—Arnold, White & Durkee

[57] ABSTRACT

A multiple-lumen intravenous catheter for critical-care applications comprises an elongated cylindrical tube. This tube has a first septum dividing the interior of the catheter into a large lumen having an elliptical cross section, and a smaller lumen having a crescent-shaped cross section. The smallest diameter of the elliptical cross section is larger than the radius of the interior of the catheter. A second septum divides the crescent-shaped lumen into two small lumens.

13 Claims, 3 Drawing Sheets

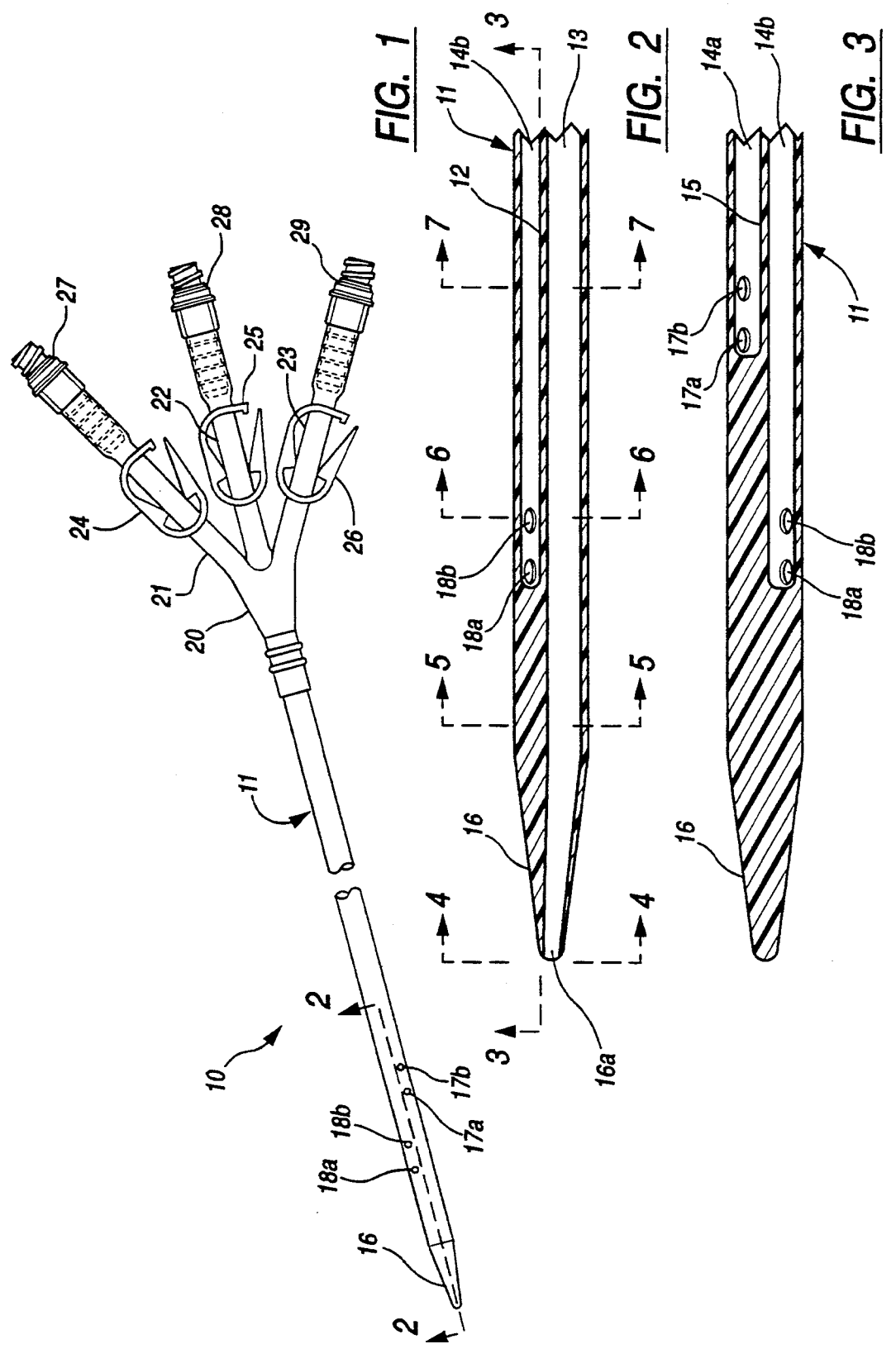

TRIPLE-LUMEN CRITICAL CARE CATHETER

FIELD OF THE INVENTION

This invention relates to catheters that are inserted into a patient's body for diagnostic or therapeutic purposes. This invention specifically relates to multi-lumen catheters that are used in the management of patients suffering from shock, trauma, dehydration or chemical or infectious circulatory collapse.

BACKGROUND OF THE INVENTION

In order to maintain adequate blood pressure in critical care patients, crystalloid or colloid solutions must be infused at a fast rate. It is also essential that the rate of infusion is not so high as to produce a circulatory overload. The adequacy of infusion is best judged by the hydrostatic pressure in the vein into which the fluids are infused. The patient also needs to be given medications which at times cannot be mixed in the infusion bottle because of incompatibility. Such medications are injected from a syringe through a separate lumen and released at a different site in the vein for immediate dilution by the blood stream. It is also necessary to obtain samples of the patient's blood from time to time to make diagnoses or to gauge the patient's progress. The triple-lumen catheter of the present invention is intended to be tailored to the specific requirements of such patients.

Numerous critical-care catheters are already known, but they have various disadvantages.

Howes U.S. Pat. No. Re. 31,873 describes a triple-lumen catheter with a transversely cut tip and intended to be introduced through a hypodermic needle. The catheter contains three identical tubes enclosed into a circular tube that forms the body of the catheter. The longest lumen opens at the end of the catheter while the other two lumens open at staggered locations. Another embodiment uses a cylindrical tube trisected by three radial septa into three identical lumens so that all the lumens can be used interchangeably for the intended functions. Commercial catheters similar to those described in the Howes patent have one of the lumen slightly larger than the other two, but large areas of dead space between the lumens makes this catheter relatively inefficient.

Howes U.S. Pat. No. 4,894,057 describes a triple-lumen catheter of construction similar to the above and containing three circular lumens of equal size for use interchangeably, or with one lumen slightly larger than the other two. Grooves are formed on the surface of the catheter extending from the exit port of each lumen to the end of the catheter to minimize the mixing of the fluid infused through the lumens. Traditionally the existence of grooves on catheter surfaces has been avoided because of the potential to form clots.

Another previously proposed triple-lumen catheter uses a circular tube that contains three radial septa arranged in a spiral form within the tube. Each lumen is therefore a spiral lumen, and the three lumens have identical cross sections. This spiral flow path offers a significant resistance to fluid flow.

Mahurkar U.S. Pat. No. 5,221,255 describes a triple-lumen catheter consisting of a circular tube divided into a semicircular lumen for fluid infusion in hypotensive patients, and two quarter-circle lumens for injection of fluids or obtaining samples of blood or measurement of hydrostatic pressure. This is the first example of a triple-lumen catheter for performing the critical functions discriminately. The septa contained in the circular tube form a "T" beam that makes the catheter kink resistant. The dead space wasted in the circular lumen catheter is also eliminated. This device satisfies the requirements of a triple-lumen critical care catheter, but the fluid flow efficiency is not as high as desired for many critical care applications.

SUMMARY OF THE INVENTION

The purpose of the present invention is to provide a superior triple-lumen catheter with respect to optimization of size, fluid mechanical efficiency and ability to infuse large volumes of fluids at a high rate. A related object is to provide such a catheter that has the structural stability required for inserting the catheter into deep seated and curved central veins.

When critically ill patients requiring fluid resuscitation arrive in the emergency room or develop shock in the operating room, fluids are usually infused from an I.V. fluid source hung from a height of three to four feet. This gravity head usually provides a good infusion rate. However, occasionally the infusion bottles need to be externally compressed to enhance the infusion rate. The compression devices are not universally available, however, and thus it is desirable that the catheter be efficient enough to provide adequate flow by gravity alone. The present invention provides an efficient circular or elliptical flow geometry that offers the least flow resistance. The circular or elliptical infusion cavity is enlarged to increase the flux by the fourth power of the radius. It occupies a major portion of the cross section of the triple-lumen catheter. The present invention also provides a small catheter which is fluid mechanically efficient and permits high-volume infusions by the gravity gradient alone.

The other two lumens are semicrescentic and have no constraints with respect to gradient. Medications can be injected by syringe, and samples of blood can be aspirated by manual force. These functions do not depend on the gravity head. Hydrostatic pressure can also be measured through the smaller lumens, and if necessary it can also be measured via the larger circular or elliptical infusion lumen by momentarily connecting the larger lumen line to a nanometer via a stopcock.

Another attribute of this invention is that it can permit multiple infusions of medications that are incompatible with each other but can be infused individually through the independent lumens and released at axially staggered points in the high flow circulatory system. This dilutes the medications significantly and avoids any incompatibility problems.

Another aim of the present invention is to provide a catheter with lumens that are formed by septa constituting common walls. This avoids the dead spaces present in currently existing multi-lumen catheters containing circular lumens.

Yet another aim of the present invention is to provide a catheter with lumen geometry that is dictated by the therapeutic regimen of managing critically ill patients.

Other objects and advantages of the invention will become apparent upon reading the following detailed description and upon reference to the accompanying drawings.

The multi-lumen catheter of this invention is a flexible cylindrical tube made of polymeric material whose outer circumference on a transverse section forms a single closed plain curve at any point along its course. The cylindrical tube encloses a smaller circular or elliptical co-tangential tube that has an inside diameter substantially larger than the radius of the cylindrical tube. The co-tangential location of the smaller circular or elliptical tube forms a crescentic space between the two tubes. The crescentic lumen is bisected by a partition that joins the outer surface of the inner tube with the inner surface of the outer. In the preferred embodiment the tangential contact and axis of the bisecting partition lie in a common diametric plane. The inner circular tube is thus anchored at both ends of the diametric plane to provide stability to the catheter structure and prevent kinking of the catheter. This transverse cross-sectional configuration extends along the entire length of the catheter from the proximal end to the digital end of the shortest of the three lumens.

Extension tubes for the three lumens may be attached directly to expanded proximal ends of the lumens or via an insert molded connector. The extension tubes carry female luer end to facilitate the attachment to I.V. lines or syringes. The largest lumen extends along the entire length of the catheter and opens at the apex of a conical tapered tip that merges with the outer circumference of the outer cylindrical tube. An additional opening is provided in the side wall of the catheter to communicate with a distal end portion of the large lumen to permit exit of the fluid and to prevent pressure build-up. The distal ends of the two semi-crescentic lumens also open through the side wall of the catheter and are axially separated. The distal ends of all three lumens enter the vein and are in fluid communication with venous blood and the extension tubes. The catheter is also stabilized by the tangential contact of the inner and outer tubes along the entire length of the catheter.

BRIEF DESCRIPTION OF THE DRAWINGS

FIG. 1 is a perspective view of a triple-lumen catheter embodying the present invention;

FIG. 2 is an enlarged longitudinal section taken along a diameter of the distal portion of the catheter of FIG. 1, parallel to and through the flat partition inside the catheter, as generally illustrated by line 2—2 in FIG. 1;

FIG. 3 is a longitudinal section taken along line 3—3 in FIG. 2;

DETAILED DESCRIPTION OF THE PREFERRED EMBODIMENTS

Figure 7:
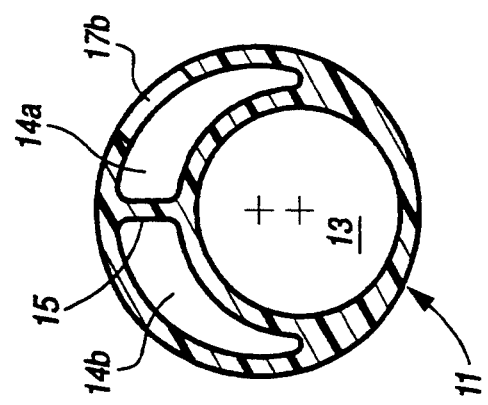
FIG. 7 is a section taken generally along line 7—7 in FIG. 2.
Figure 6:
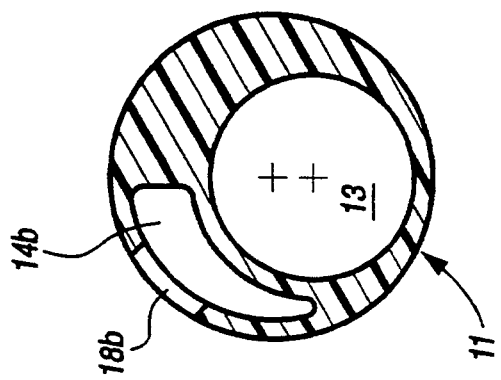
FIG. 6 is a section taken generally along line 6—6 in FIG. 2.
Figure 5:
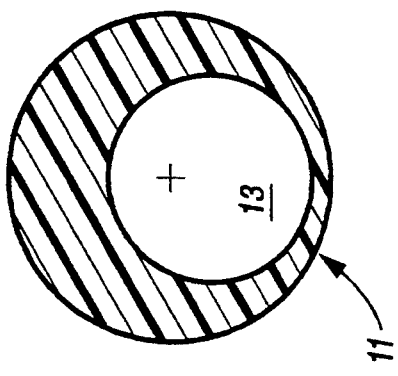
FIG. 5 is a section taken generally along line 5—5 in FIG. 2.

While the invention is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

Turning now to the drawings and referring first to FIGS. 1–7, there is shown a triple-lumen critical-care catheter 10 which includes an elongated cylindrical tube 11 made of polyurethane. The tube 11 encloses a co-tangential arcuate septum 12 which divides the interior of the tube 11 into a cylindrical lumen 13 having a circular transverse cross-section, and a cavity 14 having a crescent-shaped transverse cross-section, and a planar septum 15 which bifurcates the crescent-shaped cavity 14 to form two smaller lumens 14a and 14b.

The arcuate septum 12 in combination with the co-tangential portion of the tube 11 form an inner tube defining the large cylindrical lumen 13 having a circular transverse cross section along the entire length of the catheter. The inside diameter of this circular lumen 13 is substantially larger than the inside radius of the tube 11 so as to provide a large lumen cross-section capable of high fluid infusion rates. In addition to the large cross-sectional area of the circular lumen 13, the circular geometry minimizes fluid flow resistance. The point of cotangency between the tube 11 and the inside wall of the lumen 13 lies within the diametral plane containing the planar septum 15, to resist collapse of the lumen 13 and kinking of the catheter. In addition, the catheter walls are relatively thick where the arcuate septum 12 joins the outer cylinder, forming rounded ends on the crescent-shaped cavity 14. This combination of features in the interior geometry of the catheter provides a stable structure which further contributes to the desired high fluid infusion rates. The two semi-crescent-shaped lumens 14a and 14b have much smaller transverse cross-sections than lumen 13 and can be used for a variety of different purposes, such as injection or infusing liquid medications or other fluids into the patient, withdrawing blood samples from the patient, or monitoring the hydrostatic pressure in the vein of the patient.

Figure 4:
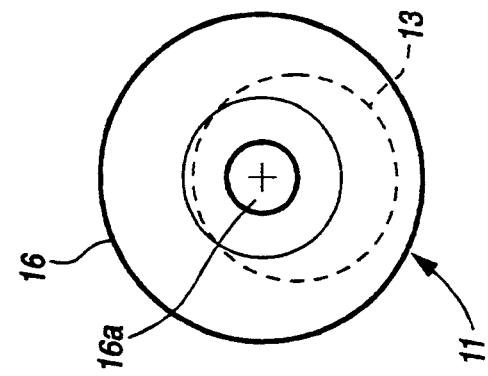
FIG. 4 is an end elevation taken at the distal end of the catheter portion shown in FIG. 2, as illustrated by line 4—4 in FIG. 2.
Figure 11:
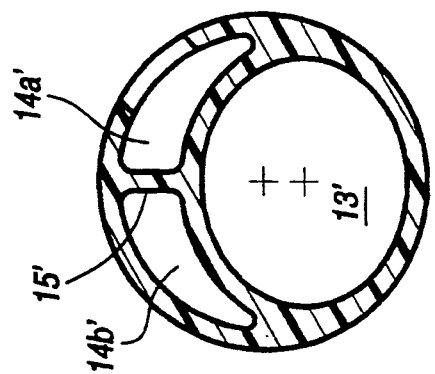
FIG. 11 is a section similar to FIG. 7 of the modified catheter.
Figure 10:
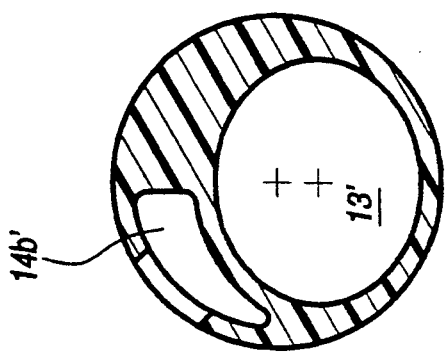
FIG. 10 is a section similar to FIG. 6 of the modified catheter.
Figure 9:
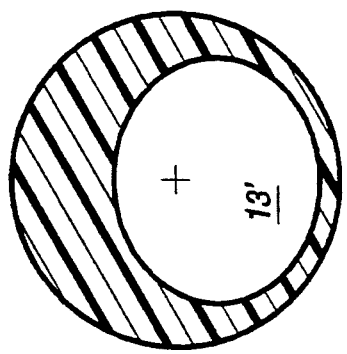
FIG. 9 is a section similar to FIG. 5 of the modified catheter.
Figure 8:
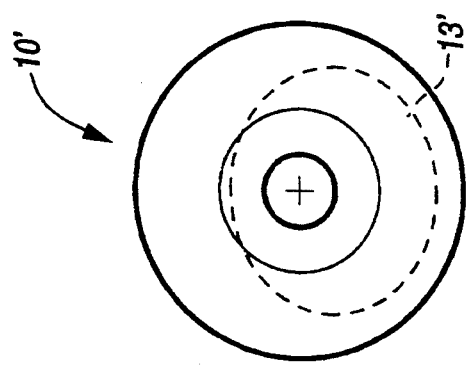
FIG. 8 is an end elevation, similar to FIG. 4, of a modified catheter embodying the invention.

At the distal end of the catheter, the exterior surface of the cylinder 11 merges into a smoothly tapered conical tip 16. On the inside, the circular lumen 13 extends longitudinally all the way through the tip 16, bending and tapering slightly as it passes through the tip so that it opens at 16a near the center of the distal end of the conical tip, as can be seen in FIGS. 2 and 4.

In order to provide a longitudinal spacing between the distal openings of the three lumens, the lumens 14a and 14b are terminated at openings 17a, 17b and 18a, 18b in the side wall of the catheter. The multiple openings permit fluid to enter or exit the lumens freely in the event of a blockage of one of the openings against the wall of the vein into which the catheter 10 is inserted.

At the proximal end of the catheter 10, the three lumens open into a connector or hub 20 which forms three internal passageways communicating with the proximal ends of the catheter lumens. The distal ends of the hub passageways may be shaped so that they form extensions of the catheter lumens 13, 14a and 14b. The passageways diverge from each other and assume a circular cross section as they extend toward the proximal end of the hub, and they also increase in cross-sectional area. The hub 20 is preferably molded in place on the end of the catheter, using mold inserts to form the hub passageways. Alternatively, the walls of the catheter lumens may be expanded at the proximal end of the catheter to fit over corresponding portions of a preformed hub with the inside walls of the catheter lumens being bonded to the mating walls of the hub 20.

The hub 20 forms three extension tubes 21, 22 and 23 which are long enough to receive conventional clamps 24, 25 and 26 for opening and closing the respective tubes. The extension tubes 20–23 are relatively soft and flexible, so that they can be easily manipulated and also easily closed by the pressure of the clamps 24–26. The clamps serve as on-off valves for controlling the flow of fluids between the catheter and associated equipment. The proximal ends of the tubes 20–23 are joined to respective ferrules formed as integral parts of luer connectors 27, 28 and 29. The luer connectors serve as coupling means for coupling the proximal ends of the extension tubes to the flexible tubes leading to the extracorporeal equipment.

FIGS. 8–11 illustrate a modified catheter 10' in which the large lumen 13' has an elliptical rather than circular cross section. The minor axis of the ellipse is in the same plane as the planar septum 15', while the major axis of the ellipse is perpendicular to the plane of the septum 15'. The minor inside diameter of the elliptical lumen 13' is about the same length as the diameter of the circular lumen 13 in FIGS. 1–7, but the major inside diameter of the lumen 13' is substantially longer than the diameter of the lumen 13. Consequently, the overall cross-sectional area of the lumen 13' is increased, which in turn increases the fluid infusion rate through this lumen.

I claim:

1. A multiple-lumen intravenous catheter for critical-care applications, said catheter comprising an elongated cylindrical tube having a first septum dividing the interior of the catheter into a large lumen having an elliptical cross section, and a smaller lumen having a crescent-shaped cross section, the smallest diameter of said elliptical cross section being larger than the radius of the interior of the catheter, and a second septum dividing the crescent-shaped lumen into two small lumens.

2. The catheter of claim 1 wherein said cylindrical tube and said large lumen are co-tangential.

3. The catheter of claim 1 wherein the transverse cross section of said large lumen is circular.

4. The catheter of claim 1 wherein said first septum is arcuate and said second septum is planar.

5. The catheter of claim 1 wherein said cylindrical tube and said elliptical lumen are co-tangential, said second septum is planar and lies in a diametral plane passing through the point of co-tangency between said tube and said elliptical lumen.

6. The catheter of claim 1 wherein the major axis of the elliptical cross section of said larger lumen is perpendicular to a diametral plane containing said second septum.

7. The catheter of claim 1 which includes a hollow conical tip on the distal end of said tube, the outside surface of said conical tip merging smoothly with the outside surface of said tube, and the inside surface of said conical tip merging smoothly with the inside surface of said large lumen, the distal ends of the other two lumens being longitudinally spaced from the distal end of said tip and from each other.

8. The catheter of claim 4 wherein said conical tip forms a solid connection from the distal ends of said other lumens to the distal end of said tip.

9. The catheter of claim 1 wherein said large lumen extends all the way through the distal end of said tube, said other lumens terminate at apertures spaced longitudinally from the distal end of said tube.

10. A method of using a multiple-lumen intravenous catheter with a critically-ill patient, said multiple-lumen catheter including an elongated cylindrical tube having a first septum dividing the interior of the catheter into a large lumen having an elliptical cross section, and a smaller lumen having a crescent-shaped cross section, the smallest diameter of said elliptical cross section being larger than the radius of the interior of the catheter, and a second septum dividing the crescent-shaped lumen into two small lumens, the method comprising the steps of:

inserting the catheter into a vein of a patient;
infusing a fluid into the vein through the large lumen; and
monitoring the hydrostatic pressure in the vein through one of the other lumens.

11. A method of using a multiple-lumen intravenous catheter with a critically-ill patient, said multiple-lumen catheter including an elongated cylindrical tube having a first septum dividing the interior of the catheter into a large lumen having an elliptical cross section, and a smaller lumen having a crescent-shaped cross section, the smallest diameter of said elliptical cross section being larger than the radius of the interior of the catheter, and a second septum dividing the crescent-shaped lumen into two small lumens, the method comprising the steps of:

inserting the catheter into a vein of a patient;
infusing a first fluid into the vein through the large lumen;
monitoring the hydrostatic pressure in the vein through one of the other lumens; and
infusing a second fluid into the vein through the third lumen.

12. A method of using a multiple-lumen intravenous catheter with a critically-ill patient, said multiple-lumen catheter including an elongated cylindrical tube having a first septum dividing the interior of the catheter into a large lumen having an elliptical cross section, and a smaller lumen having a crescent-shaped cross section, the smallest diameter of said elliptical cross section being larger than the radius of the interior of the catheter, and a second septum dividing the crescent-shaped lumen into two small lumens, the method comprising the steps of:

inserting the catheter into a vein of a patient;
infusing a first fluid into the vein through the large lumen;
monitoring the hydrostatic pressure in the vein through one of the other lumens; and
injecting a medication into the vein through the third lumen.

13. A method of using a multiple-lumen intravenous catheter with a critically-ill patient, said multiple-lumen catheter including an elongated cylindrical tube having a first septum dividing the interior of the catheter into a large lumen having an elliptical cross section, and a smaller lumen having a crescent-shaped cross section, the smallest diameter of said elliptical cross section being larger than the radius of the interior of the catheter, and a second septum dividing the crescent-shaped lumen into two small lumens, the method comprising the steps of:

inserting the catheter into a vein of a patient;
infusing a first fluid into the vein through the large lumen;
monitoring the hydrostatic pressure in the vein through one of the other lumens; and
withdrawing blood from the vein through the third lumen.

* * * * *